April 6, 1971 H. DEN OUDEN ET AL Plant Pat. 3,038

BARBERRY SHRUB

Filed Feb. 17, 1969

INVENTORS.
HENDRIK DEN OUDEN,
FRITS DEN OUDEN,

By Edmond J. Shanahan
ATTORNEY.

United States Patent Office

Plant Pat. 3,038
Patented Apr. 6, 1971

3,038
BARBERRY SHRUB

Hendrik den Ouden and Frits den Ouden, Boskoop, Netherlands, assignors to Monrovia Nursery Company, Azusa, Calif.

Filed Feb. 17, 1969, Ser. No. 800,010
Int. Cl. A01h *5/00*
U.S. Cl. Plt.—58 1 Claim

Figure 1:
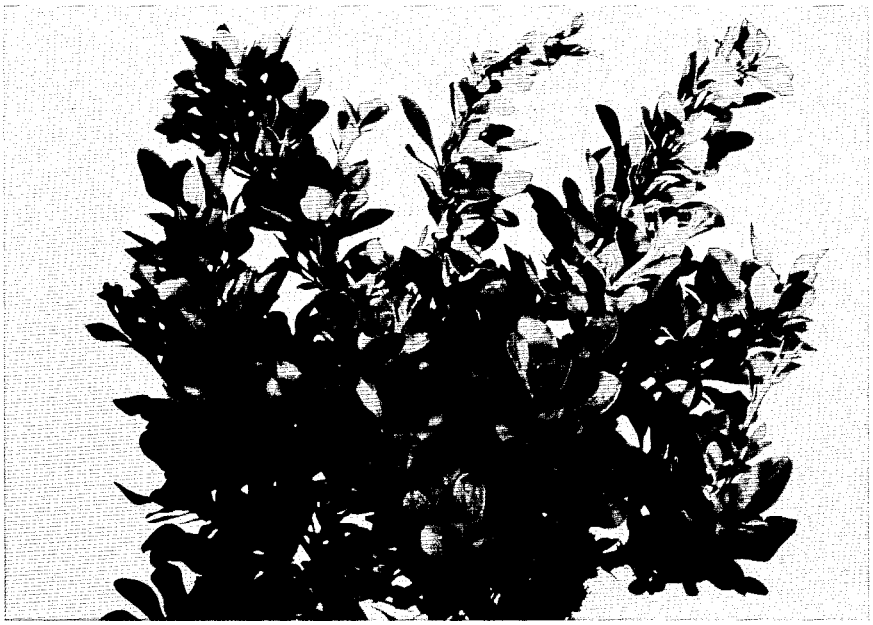

The present invention relates to a new and distinct variety of the Berberis genus commonly called barberry shrub. It is characterized as to novelty by its compact densely branched habit of growth, its ability to maintain its spreading globular shape with a minimum of pruning and the pleasing green color of its foliage.

The plant originated by chance as a sport seedling, which we discovered as a chance seedling found growing in a bed of 1,000 *Berberis thumbergi atropurpurea nana* (known in Holland as "Little Favorite" and in the United States as "Crimson Pygmy." Subsequent plants have been produced by asexual propagation, all showing the same characteristics. The novel barberry will not produce true from seed.

The specific known variety most like the new variety is *Berberis thunbergi atropurpurea nana* "Crimson Pygmy" the foliage of which is red, while that of the new variety is green. Also, the new variety is more spreading and globular in shape. Another known variety which bears similarity to the new variety is *Berberis buxifolia nana* but the variety of this invention resembles *buxifolia nana* only in its shape the leaves of *Berberis buxifolia nana* are shaped differently and the nodes of the new variety are closer together.

The new variety has some resemblances to *Berberis thunbergi minor,* which like the new variety is deciduous. However, *Berberis thunbergi minor* presents a radically different appearance, since: (a) its leaves are only 7/16" long (about half the length and about one-fourth the area of the new variety) (b) it is a much smaller plant than the new variety at every stage of growth and at maturity, being about half the size of the new variety at each stage and at maturity and (c) its leaves are not spatulate, as are those of the new variety.

Figure 2:
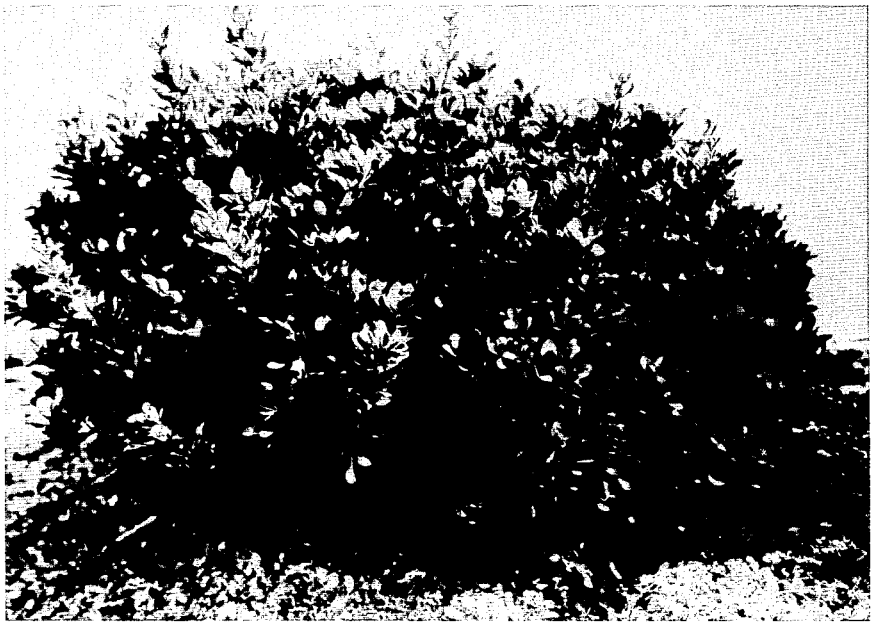

In the drawings (color photographs):

FIG. 1 is a picture of a five year old shrub, showing the characteristic appearance of the new variety; and FIG. 2 is a picture of the foliage of the new variety.

A detailed description of the new variety follows and to facilitate identification of the important colors, the color terminology adopted by the British Horticultural Color Charts has been followed.

*The plant*

Parentage: Chance seedling, resulting from open pollenization. Pollen and seed parents are unknown.

Growth: The plant is of moderately vigorous, compact, spreading habit of growth. The plant is comprised of multiple branches from the base; it does not have any central leader or trunk. The ultimate height and spread of the plant is not known. Plant shown in the picture is five (5) years old and has a height of from twelve (12) to fourteen (14) inches and a spread of from twenty-two (22) to twenty-four (24) inches.

Branches: New growth at first a light green quickly changing to a light reddish brown, changing to a dark reddish brown at maturity. Branches are arching and spreading from the base.

Growth habit: Branching starts from ground level and is arching and spreading.

Foliage: The leaves are of good substance and glossy. New leaves are Scheeles Green 860 on the upper surface and Scheeles Green 860/3 underneath. Mature leaves are slightly darker than Spinach Green 0960 on the upper surface and are Spinach Green 0960/2 beneath. Leaves are deciduous, turning to grayish-green before dropping.

Shape: The leaves are best described as being spatulate in shape with an occasional leaf being obicular. The leaves are from ¾ to 1 and ¼ inch in length and from 5/16 inch to ½ inch in width. Edges of leaves are entire, tip or apex is mucronate, spine soft. Leaf base along main rib is slightly grooved. Petiole ⅛ inch to 3/16 inch long and is grooved. Leaves are clustered at the nodes in groups of from six (6) to twenty (20). Nodes are alternate on the branches.

Veins: Few, not prominent, main rib recessed on upper surface, slightly raised on underside. Pale green above and slightly darker than Spinach Green 0960/2 beneath.

Spines: One at each node. Spines are from 3/16 to ¼ inch in length.

*Flowers*

The plant flowers in the late spring with an occasional flower cluster appearing as late as July.

Form: Of the usual form and shape of the Berberis genus, the calyx of six (6) distinct sepals, corolla of six (6) distinct petals, stamens six (6), pistil one (1). Sepals and petals are obovate in shape. Sepals about 3/16 inches in length and about the same in width at the widest part. Petals are the same size and shape as the sepals.

Color: Sepals and petals are all one color, Primrose Yellow 601/2.

Inflorescense: Flower clusters are axillary and three (3) different types were observed.

(1) Fasciled with 3 to 9 flowers.
(2) Umbel like peduncle ⅜ inch long. Usually 5 flowers.
(3) Umbel of 5 flowers with 3 flowers subtended at base of peduncle.

Flowers are considered to be sterile as no fruit set on any of the plants that flowered.

I claim:

1. A new and distinct variety of genus Berberis shrub, substantially as shown and described, characterized by a combination of features not found combined in prevously known members of the genus, these features being compact globular branching, foliage of a green color as described, and a leaf structure and shape unusual in Berberis.

No references cited.

ROBERT E. BAGWILL, Primary Examiner